United States Patent
Quakenbush et al.

[11] Patent Number: 5,847,240
[45] Date of Patent: Dec. 8, 1998

[54] PROCESS FOR REDUCING TETRANITROMETHANE IN COMPOSITIONS CONTAINING NITROAROMATIC COMPOUNDS

[75] Inventors: Allen B. Quakenbush, Lake Charles; Buford T. Pennington, Sulfur, both of La.

[73] Assignee: Arco Chemical Technology, L.P., Greenville, Del.

[21] Appl. No.: 824,654

[22] Filed: Mar. 24, 1997

Related U.S. Application Data

[60] Provisional application No. 60/015,544, Apr. 16, 1996.
[51] Int. Cl.$^6$ .................................................. C07C 205/00
[52] U.S. Cl. ........................ 568/939; 568/935; 568/932; 568/940
[58] Field of Search ..................... 568/935, 939, 568/940, 932

[56] References Cited

U.S. PATENT DOCUMENTS

| | | |
|---|---|---|
| 1,632,959 | 6/1927 | Gartner . |
| 4,003,977 | 1/1977 | Gilligan et al. . |
| 4,713,232 | 12/1987 | Chin et al. . |
| 5,171,455 | 12/1992 | Wang et al. . |
| 5,589,037 | 12/1996 | Guggenheim et al. . |

FOREIGN PATENT DOCUMENTS

| | | |
|---|---|---|
| Sho 57-302 | 6/1977 | Japan . |
| Sho 57-156445 | 3/1981 | Japan . |
| 57-15645 A | 9/1982 | Japan . |

*Primary Examiner*—Michael L. Shippen
*Attorney, Agent, or Firm*—Dale Lynn Carlson; Wiggin & Dana

[57] ABSTRACT

A process is disclosed for removing a light organic compound from a liquid composition comprising said light organic compound in admixture with a nitroaromatic compound, said light organic compound having a partial vapor pressure in said composition that is greater than the partial vapor pressure of said nitroaromatic compound in said composition, said process comprising contacting said composition with steam or a gas to cause at least a portion of said light organic compound to pass out of said composition and into admixture with said steam or gas.

11 Claims, No Drawings

PROCESS FOR REDUCING TETRANITROMETHANE IN COMPOSITIONS CONTAINING NITROAROMATIC COMPOUNDS

This is a provisional Application Ser. No. 60/015,544 filed Apr. 16, 1996.

FIELD OF THE INVENTION

This invention relates generally to tetranitromethane, and, more specifically, to a process for separating tetranitromethane from a nitroaromatic compound-containing, tetranitromethane-containing composition.

BACKGROUND OF THE INVENTION

During the synthesis of nitroaromatic compounds (also referred to as "aromatics"), such as dinitrotoluene ("DNT"), trinitrotoluene ("TNT"), and dinitrobenzene ("DNB"), a small amount of the aromatic feed stock is oxidized to produce undesirable byproducts such as nitrocresols and nitrophenols. Depending upon the reaction conditions, including acid strength and temperature, these byproducts can be further oxidized to form other byproducts. One such other byproduct is tetranitromethane ("TNM").

The presence of relatively high levels of TNM byproduct during processing to produce the desired nitroaromatic compound can pose a safety hazard. More specifically, TNM that "phases out" and is present in high localized concentrations, or precipitated from the process stream, can render nitroaromatic compounds shock sensitive. This shock sensitivity has resulted in explosions in the past. The risk of an explosion is minimized when TNM is maintained at low concentrations. Therefore, monitoring and managing the amount of TNM in order to insure a low concentration of TNM in a nitroaromatic compound(s) manufacturing process are important safety considerations. New methods that facilitate maintaining the TNM in such low concentrations would be highly desired by the nitroaromatics manufacturing community.

In addition to the safety issue discussed above, the presence of significant amounts of TNM in a nitroaromatics product can cause a product quality problem to occur during storage of the product prior to its use. This product quality problem results from the gradual hydrolysis of the TNM byproduct to trinitromethane and nitric acid, often rendering the nitroaromatics product out of specification with respect to maximum allowable nitric acid content. Nitric acid in a nitroaromatic can greatly increase the product's corrosivity and adversely affect other downstream uses of the product. Therefore, new methods that facilitate maintaining the TNM in low concentrations would be highly desired by the nitroaromatics manufacturing community to insure product quality with respect to the nitric acid content.

The present invention addresses the process safety and product quality concerns identified above by providing a facile method for separating TNM and/or other light organic compounds from a nitroaromatics-containing composition.

SUMMARY OF THE INVENTION

In one aspect, the present invention relates to a process for removing a light organic compound from a liquid composition comprising said light organic compound in admixture with a nitroaromatic compound, said light organic compound having a partial vapor pressure in said composition that is greater than the partial vapor pressure of said nitroaromatic compound in said composition, said process comprising contacting said composition with steam or a gas (preferably air or an inert gas) to cause at least a portion of said light organic compound to pass out of said composition and into admixture with said steam or gas.

In another aspect, the present invention relates to a process for removing tetranitromethane from a composition comprising (and advantageously consisting essentially of) tetranitromethane and dinitrotoluene which comprises contacting said composition with steam or a gas (preferably air or an inert gas) to cause at least a portion of said tetranitromethane to pass out of said composition and into admixture with said steam or gas.

These and other aspects will become apparent upon reading the following detailed description of the invention.

DETAILED DESCRIPTION OF THE INVENTION

It has now been surprisingly found in accordance with the present invention that both process safety and product quality problems, otherwise associated with the presence of TNM in an aromatics production process stream, are obviated by a straightforward process for removing the TNM from the aromatics product. More specifically, removal of the TNM is effected by contacting the aromatics product with an inert gas or steam.

Although the process of the present invention is particularly advantageously employed to remove TNM from a composition containing the TNM and a nitroaromatics compound, the present invention is broadly applicable to the removal of other so-called "light compounds" or "lights". The "lights" are defined herein as those compounds (advantageously organic compounds), present in a nitroaromatics-containing composition, having a partial vapor pressure that is higher than the partial vapor pressure of the nitroaromatic compound in the composition. As used herein, the term "nitroaromatic compound" or "nitroaromatic(s))" is intended to include those compounds containing at least one aromatic ring wherein the compound contains between 6 and 20 carbon atoms.

Although not wishing to be bound by any particular theory, it is believed by the present inventors that the process of the present invention provides a solution to a nitroaromatics product quality problem that otherwise tends to occur during storage of a TMN-containing, nitroaromatics product. The product quality problem is caused by a higher than expected level of nitric acid in the product. Surprisingly, the cause this level of nitric acid has been found by the present inventors to be attributable to hydrolysis of the TNM in accordance with the following equation:

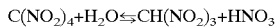

$$C(NO_2)_4 + H_2O \rightleftharpoons CH(NO_2)_3 + HNO_3$$

TNM is a byproduct of oxidation during synthesis and a portion of it carries forward with the organic product. Water, although effective as a wash to remove nitric acid from the nitroaromatics product, is ineffective in the extraction of TNM from the nitroaromatics, so a means to remove the TNM is needed if the final nitric acid concentration is to be low. Otherwise, a slow hydrolysis sets in accordance with the equation given above, causing an unacceptably high level of nitric acid to form in the product during storage of the nitroaromatics product, rendering a product having an undesirable concentration of nitric acid.

The present invention provides an effective and economical way to remove TNM or other lights from the nitroaromatic compound-containing composition in which the TMN or other light is present. Contacting the composition, containing the nitroaromatic compound, with an inert vapor or gas causes a great reduction in the level of TNM and/or other light present in the composition, thus providing a product that is not subject to becoming a product with an undesirable concentration of nitric acid during storage due to a high nitric acid content.

Although any gas that can be employed safely in the specific plant environment can be used in accordance with the present invention, inert gases, such as nitrogen, helium or argon, are preferred. Nitrogen is particularly preferred in view of its relative low cost. Other gases such as air are suitably employed, subject to any plant safety concerns attributable to the oxygen present in the air. Steam can also be effectively used, and steam has been found to be particularly advantageous in the process of the present invention.

Contacting of the TNM (or other light(s)) laden product with the steam or inert gas is suitably effected using a gas/liquid or vapor/liquid contacting device, such as a packed or unpacked column. The nitroaromatics liquid is suitably fed into the top of the column, and the inert gas or water vapor is fed at the bottom of the column. The column can be a single step, multistage device, and the column is suitably employed in a counter-current or co-current flow configuration. The column can, if desired, employ trays, packing, or other means to provide effective contacting of the vapor rising vapor against the falling liquid. The product is stripped of part or all of the TNM, and the TNM is passed into the vapor or gas, thus eliminating the risk of downstream impact on product quality due to nitric acid formation from the TNM that would otherwise be present in the product.

The amount of inert gas or vapor used can be traded off against the number of counter current stages used. Generally, the optimum number of contacting stages will be 2 to 10, with the most preferred around 4. The economy of equipment cost is balanced against the operating cost of downstream processing of the gas or vapor. Typically, steam consumption can be quite low. For DNT, the 0.2 pounds of steam per pound of organic fed can effectively reduce 500 ppm TNM to less than 50 ppm in about 4 stages. Advantageously, the amount of TNM remaining in the product is less than 150 ppm, preferably no greater than 50 ppm, more preferably between 25 ppm and 50 ppm. Additional stages can be used to decrease the amount of TNM to a non-detectable level of essentially zero, e.g., one ppm or less. Steam usage will be increased if the amount of stages are reduced or the initial TNM concentration is increased.

The temperature range is set at the low end by the freezing point of the nitroaromatic and the upper end by its safe operating temperature (i.e., keep it safely below its operating temperature to avoid decomposition of the product or byproduct). For the case of DNT as the nitroaromatic compound, lower pressures are more efficient in the removal of TNM. The relationship between operating pressure and operating temperature is such that, for removal of TNM or other lights from DNT, a useful temperature range of between 58 degrees Centigrade and 130 degrees Centigrade corresponds to a useful pressure range of between about 2.5 psia and about 40 psia. Below a temperature of about 58 degrees Centigrade, there are possible viscosity problems and a risk of freezing for the DNT/TNM mixture; and above a temperature of about 130 degrees Centigrade, there is a product decomposition risk. Well within this operable range, removal of TNM from DNT is advantageously effected at a reduced operating pressure of about 8 psia, thus providing an operating temperature of about 87° C. Such an operating temperature is well above the freezing point of DNT, and such an operating pressure provides more efficient, and hence more effective, separation of TNM than higher operating pressures would.

The isomeric DNT mixture typically utilized in the manufacture of toluene diisocyanate contains about 76% of 2,4-DNT, about 19% of 2,6-DNT, and about 5% of other isomers. The vapor pressure of this isomeric DNT mixture at 60° C. is 0.02 mm of Hg. At 118° C., this mixture's vapor pressure is 1 mm of Hg, and at 130° C. the vapor pressure reaches 2 mm of Hg. When the partial pressure of any light component (nitric acid, TNM or trinitromethane or other light components) exceeds the vapor pressure of the organic, then stripping will be effective in accordance with the process of the present invention.

Illustrative of the efficiency of the removal of TNM from DNT is the following chart:

| Lb(s) Used per 100 Lbs DNT Processed | Removal % with Steam | Removal % with Nitrogen |
|---|---|---|
| Single Stage Removal Efficiency (Steam Versus Nitrogen) for TNM from DNT Operating Pressure: 8 PSIA | | |
| 1 | 10.8 | 8.8 |
| 5 | 40.3 | 26.4 |
| 10 | 57.8 | 42.0 |
| 50 | 87.5 | 85.1 |
| 100 | 93.4 | 94.3 |

The numbers in the above chart are calculated based upon measurements of DNT volatility and TNM's relative volatility over DNT. The DNT illustrated in this chart is the above-described DNT isomeric mixture. Beyond the single stage illustration provided in the chart above, the efficiency increases with the addition of stages.

In a stripping column, the overhead portion of the product exiting the stripping column is suitably fed to other plant operations using water and nitric acid to recover any acid or DNT stripped along with the TNM. At this point, it useful to maintain TNM in the vapor phase. TNM has a low solubility in aqueous systems, so keeping it in the vapor phase prevents it from saturating the liquid and forming a second phase. Introducing TNM bearing steams into units with high water concentrations is most preferable. It is relatively easy to maintain the TMN in the vapor phase since TNM has a surprisingly high relative volatility over water, and condensing TNM into streams with high concentrations of water can only be done with great difficulty. The volatility of TNM over water can be even further enhanced, if desired, by the addition of small amounts of an inert gas such as nitrogen or air.

The following examples are intended to illustrate, but in no way limit the scope of, the present invention.

EXAMPLES

Example 1

TNM Removal from a Nitroaromatic Product Using Steam

DNT with 570 ppm of TNM was fed at the top of a stripping column at 10 grams per minute and collected at the bottom. The column had 10 trays and the pressure in the column was maintained at 200 millimeters of mercury (mm of Hg). Steam was injected into the bottom of the column at 2.8 grams per minute, contacted in countercurrent fashion with the falling DNT, and collected overhead. The TNM in the final DNT was reduced to 102 ppm.

Example 2
TNM Removal from a Nitroaromatic Product Using Nitrogen

DNT with 500 ppm TNM is fed at 10 grams per minute into the top of a packed column with 4 stages of contacting. At 400 mm Hg pressure, 4 grams per minute of nitrogen are injected into the bottom of the column. The nitrogen is contacted with the falling DNT and vented overhead. The TNM in the DNT collected at the bottom is reduced to about 10 ppm.

Example 3
TNM Removal from Water with Nitrogen

Water with 500 ppm TNM is fed at 100 grams per minute into the top of a packed column with enough contacting to provide a single stage, that is, thorough mixing of the aqueous liquid with the gas. At 200 mm Hg, 2 grams per minute of nitrogen is contacted with the falling water and vented overhead. The TNM in the water collected in the bottom is essentially free of all TNM (less than 1 ppm).

Example 4
Steam Stripping From DNT

Steam stripping of DNT was conducted in a 1 inch diameter pilot column with about 5 feet of packing (ceramic berl saddles). About 44 grams per minute of DNT (with isomeric mixture for TDI) were fed as a liquid to the top of the column and 7.7 grams per minute of steam were fed at the bottom and the two were contacted counter-currently. The following results were obtained:

| Component | Feed DNT | Stripped DNT |
| --- | --- | --- |
| TNM | 269 | 0 (<1 ppm) |
| Trinitromethane | 143 | 18 |
| Nitric Acid | 32 | 18 |

As can be seen from the above results, not only was the TNM effectively removed, but also other lights, including trinitromethane and nitric acid, were removed effectively as well.

While the invention has been described above with references to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A process for removing a light organic compound from a liquid composition comprising said light organic compound in admixture with a nitroaromatic compound, said light organic compound having a partial vapor pressure in said composition that is greater than the partial vapor pressure of said nitroaromatic compound in said composition, said process comprising contacting said composition with steam or a gas to cause at least a portion of said light organic compound to pass out of said composition and into admixture with said steam or gas.

2. The process of claim 1 wherein said gas is air or an inert gas.

3. The process of claim 2 wherein said inert gas is selected from the group consisting of nitrogen, argon, and combinations thereof.

4. The process of claim 1 wherein said light organic compound is selected from the group consisting of tetranitromethane, trinitromethane, and combinations thereof.

5. The process of claim 1 wherein said nitroaromatic compound is selected from the group consisting of mononitrotoluene, dinitrotoluene, mononitrobenzene, dinitrobenzene, trinitrotoluene and combinations thereof.

6. A process for removing tetranitromethane from a composition comprising tetranitromethane and dinitrotoluene which comprises contacting said composition with steam or a gas to cause at least a portion of said tetranitromethane to pass out of said composition and into admixture with said steam or gas.

7. The process of claim 6 wherein said gas is air or an inert gas.

8. The process of claim 7 wherein said inert gas is selected from the group consisting of nitrogen, argon, and combinations thereof.

9. The process of claim 6 wherein said contacting is effected in a stripping column at a pressure of between about 2.5 psia and about 40 psia and a temperature of between about 58 degrees Centigrade and about 130 degrees Centigrade.

10. The process of claim 6 wherein said gas is nitrogen, and wherein said nitrogen is employed in an amount of between 1 and 100 pounds per 100 pounds of said dinitrotoluene.

11. The process of claim 6 wherein said steam is employed in an amount of between 1 and 100 pounds per 100 pounds of said dinitrotoluene.

* * * * *